United States Patent [19]

Cumings

[11] Patent Number: 5,402,577
[45] Date of Patent: Apr. 4, 1995

[54] RADIOGRAPHIC INSPECTION AID

[75] Inventor: Robert C. Cumings, St. Peters, Mo.

[73] Assignee: McDonnell Douglas Corporation, St. Louis, Mo.

[21] Appl. No.: 139,587

[22] Filed: Oct. 20, 1993

[51] Int. Cl.$^6$ .................... G01B 15/00; G01B 11/27
[52] U.S. Cl. ........................... 33/286; 33/533; 33/645; 378/59; 378/205
[58] Field of Search ............ 33/534, 1 N, 229, 275 R, 33/281, 282, 286, 297, 520, 533, 644, 645, 1 A, 1 BB; 378/59, 205

[56] References Cited

U.S. PATENT DOCUMENTS

| | | | |
|---|---|---|---|
| 1,370,640 | 3/1921 | Granger | 33/1 A |
| 2,280,126 | 4/1942 | Metcalf | 33/286 |
| 2,414,733 | 1/1947 | Fuchs | 33/286 |
| 2,496,099 | 10/1950 | Leto | 33/520 |
| 2,581,431 | 1/1952 | Nelsen | 33/286 |
| 4,048,507 | 9/1977 | De Gaston | 378/205 |
| 4,053,782 | 10/1977 | Grass | 378/205 |
| 4,608,573 | 8/1986 | Paullin | 33/645 |
| 5,187,728 | 2/1993 | Vaughn | 378/59 |

*Primary Examiner*—Christopher W. Fulton
*Attorney, Agent, or Firm*—Joseph E. Walsh, Jr.

[57] ABSTRACT

The inspection aid 10 disclosed and claimed herein is characterized by a shape-mutable, radiographically non-absorptive appliance which includes an individual upper 28 and pair of lower 30 and 32 pins arranged in adjacent, right triangle relation and inserted transversely through either side of the appliance. An aspect central to the utility of the invention is the midpoint location of the upper pin between the lower pins.

14 Claims, 2 Drawing Sheets

RADIOGRAPHIC INSPECTION AID

BACKGROUND OF THE INVENTION

FIELD OF THE INVENTION

This invention relates, generally, to an angle continuing device and, more particularly, to a unitary plastic assembly intended for use as a radiographic inspection aid.

DESCRIPTION OF THE RELATED ART

Fusion welding is a term generally describing five common, albeit independently recognized, welding processes. These five processes are: Shielded Metal Arc-Welding (SMAW); Gas Tungsten Arc-Welding (GTAW); Gas Metal Arc-Welding (GMAW); Plasma/Arc-Welding (PAW); and Electron Beam Welding (EBW). By definition, welding involves the union of two or more materials by localized melting of base and filler materials which solidify during cooling to form a weld seam or joint interface.

A variety of factors, including the amount of withstandable pressure at the weld seam, and the criticality of this particular factor constitute bases that dictate which of the foregoing processes will be appropriate in a given application. In those applications where torsional sn-esses are limited as, for example, in the case of a water tower, pipeline or agricultural or industrial weld, comparatively simple and less expensive welding processes such as SMAW and GTAW are commonly used. While joint interface or weld seam integrity is an important object in every welding operation, the degree to which it is achieved varies from procedure to procedure. To a much greater degree than is possible using any of the other procedures, EBW finds application in critical cases where very low substrate distortion is required in conjunction with a very high quality fusion weld seam. EBW is conunonly used in the aircraft industry and, more particularly, in the production of high-performance aircraft components.

Electron Beam Welding (EBW), which is normally performed under vacuum conditions and in a specially designed chamber, involves penetration of the substrate material(s) at the joint interface by a dense beam of electrons. The high heat concentration from the narrow beam melts a path through the substrate(s) which closes as the beam proceeds or feeds along the seam or joint. Very low distortion, high quality welds result due principally to the controlled and efficient localization of heat and also due to the removal of contaminants from the joint interface by virtue of the vacuum environment in which the procedure is performed.

EBW applications are the most costly of the five fusion weld procedures identified above for three principal reasons. First, the procedure for performing the operation is more complex in that precision tooling is required for locating and positioning the region of the joint interface or seam relative to the welding beam. Secondly, overall procedure or run time is markedly increased because a closed system must first be established by evacuating the operation chamber to a pressure of about $5 \times 10^{-5}$ mm. Hg. prior to the commencement of welding. The third factor contributing to the considerable expense of EBW relates to the sophisticated and labor intensive method of inspecting the finished weld seam. It is within the ambit of this third factor that the invention disclosed herein resides.

Radiography, which is the well known technique of producing a photographic image of an opaque specimen by transmitting a beam of x-rays or gamma rays through the specimen onto an adjacent photographic film, finds wide application in industry and, more particularly, in the inspection of critical industrial weldments. As in the medical field (where radiographic application is pervasive), factors such as variation in thickness, density and the chemical composition of the subject specimen affect the clarity of the image produced by this process. Among others, these variables have been used in establishing factors of radiographic equivalence—which factors serve as an index of x-ray or gamma ray absorptability and, thus, the relative success with which a given material can be radiographically evaluated.

As a group of materials, metals exhibit radiographic equivalence factors which are very compatible with the use of radiography as an evaluation tool. Accordingly, many industrial weldments are tested or inspected for integrity using radiography.

As indicated above, welding typically involves the union of two or more materials by localized melting of base and filler materials which solidify during cooling to form a weld seam or joint interface. Because most welding procedures involve the use of filler materials and occur under ambient conditions, the opportunity for filler and airborne contaminants entering the weld seam is great. Such contaminants pose a considerable threat to the integrity of any given weld seam and account for the potential for marked differences in fusion degree as between any two welds. Because radiography presents the ability to look within the weldment and to observe the degree of material fusion as well as the existence of any contaminants, it has found wide application as a valuable industrial inspection method.

In most cases, traditional radiographic beam alignment methods are suitable for obtaining an image that can be used to evaluate both the degree of fusion and existence of contaminants within a given weldment. Special care and measures are required in the case of EBW weldments, however, as it is vitally important that the resulting radiograph images the entire width and depth of the subject interface.

Due to the extraordinary conditions of force and pressure which costly electron beam weldments are expected to withstand, the extent to which a given EBW interface meets exacting specification tolerances can only be evaluated if the character of the entire weld is observable.

Fundamental principles of radiography teach that the central ray emitted by a radiographical instrument is the strongest of the many rays which are emitted in conical fashion from the head of the tool. Additionally, it is known that the tungsten plate located in the head, is responsible both for transforming excited electrons into x-rays and then emitting such rays in direct linear relation to the plate. Based upon these phenomena, most industrial radiographical tools are designed to project a laser image corresponding with the central ray emitted by the radiographical tool when energized. This laser sighting feature is very, useful to the technician in approximating alignment between the central x-ray and the median point of the joint interface to be imaged. Because the technician knows the manner in which the central ray will be dispersed (as discussed above), he or she will align the weld seam to be imaged lengthwise in longitudinal relation to the x-ray emitting tungsten plate located in the head of the radiographical tool. With this configuration and the aid of the laser sighting beam, the technician is capable of ensuring reliable y-axis imaging lengthwise through the weld seam.

Obtaining x-axis imaging through the width of a given weld seam, while of equal significance in ensuring a complete width and depth radiograph, cannot be performed by the technician with any degree of consistency without the use of an x-axis alignment aid.

There exists a known prior art device which has been employed in the radiographic imaging field as a means of ensuring reliable x-axis imaging. The device comprises an aluminum alloy frame specially machined to receive a series of titanium blocks which are also specially machined. Three of the four blocks comprising the series are substantially similar in size being held within the frame by a combination of alternating, machine-tapered opposing edges and a set screw located at one end of the aluminum frame, and bored through the width thereof. The bottom surface of each of the blocks is precision machined in order that, when the blocks are properly placed and held within the aluminum frame, the bottom surfaces are flush. The fourth block, which is properly located adjacent the side of the aluminum frame opposite the set screw, is precision-machined to a considerably smaller dimension than that of the three remaining blocks. This fourth block is also distinguished from the other three in that each of its sides are in right angle relation to one and other with the exception of the upper outside corner which is chamfered. The chamfered corner is designed to indicate the side of the fourth block intended for assembly adjacent the aluminum frame.

The side of the fourth block opposite the chamfer is machine ground to mate with the similarly machine ground and non-tapered side of block three. The resulting seam, although invisible to the unaided eye, is intended to be in perpendicular relation to the aluminum frame. Moreover, the seam is designed to be placed over the median point of the width of a given weld seam during radiography in order to ensure desired 90 degree or perpendicular relation between the x-axis of the weld seam and the central ray emitted by the radiographical instrument. A determination that desired radiographic alignment exists, in accordance with the use of the prior art device, entails the discernment by the technician of a "sharp, clear" image of the space extant between the opposing sides of the third and fourth blocks. After a "sharp, clear" image is observed on the radiograph, the technician is assured that both y-axis and x-axis alignment exist as between the joint interface and the central ray emitted by the radiographical tool. Imaging of the subject interface is then performed and the resulting film studied for degree of weld fusion and the existence of any integrity-compromising contaminants.

A variety of shortcomings afflict the prior art device. Foremost is the expense of manufacture. The device described above and depicted in the accompanying drawings costs an estimated $1500 a copy to manufacture. This great expense is attributable both to the nature of the materials employed and the expense associated with machining the device to the required specifications. An additional and equally significant failing of the prior art device relates to the ease with which it can lose calibration. Simple handling can result in fluctuation of the set screw tension which ensures the required surface flushness of the bottoms of each of the four blocks as well as maintenance of the desired tight relationship between the opposing sides of blocks three and four. The invention disclosed and claimed herein overcomes these and other disadvantages in a manner not revealed by the known prior art.

SUMMARY OF THE INVENTION

In accordance with the present invention, a radiographic inspection device is provided consisting of a unitary article having inserted transversely therethrough a plurality of metal pins arranged in adjacent right triangle relation. The device is further characterized in that it exhibits a flat base aspect that is parallel to the transversely mounted pins.

In practice, the invention is employed as an angle alignment tool which assists in ensuring that x-rays aimed at weldments during inspection, penetrate the weld seam at an angle of approximately 90 degrees measurable against the surface of the weld along both its length and width. Specifically, in most industrial weld inspection contexts, a system is established whereby the head aspect of an overhead radio graphing machine is positioned above a receiving table upon which is placed the material or component containing the weld seam that requires inspection. Initially, the component is positioned on the table such that the length of the weld seam is longitudinally aligned with the tungsten plate contained in the head of the machine. Next, the laser beam sighting feature is activated and aimed at the central region of the weld. Because the x-ray emitting head of the machine has already been aligned lengthwise with the weld seam, a procedure is required for ensuring that the head is also aligned transversely across the width of the weld. By providing for both width and length alignment of the x-ray with respect to the interface, an image can be expected that covers both the full width and depth of the joint interface. Such an image then serves as a reliable tool for actually inspecting the weld seam for undesirable microporous structures and the existence of weld seam contaminants that pose a threat to critical-application weld integrity.

The procedure for ensuring the transverse alignment of the emitted x-rays along the width of the weld seam involves positioning the base of the instant device over a recently welded but pre-grinded and surface smooth joint interface prior to radiography such that the individual upper pin is essentially central to the weld width and also in longitudinal relation with the weld length. An image is then made employing the instant device. Because of the relative absorptability of the materials used in the invention, the radiograph will usually comprise a picture of three parallel lines representing each of the pins transversely mounted within the device. The distance between the parallel lower pins is computed in direct relation to the degree of tolerance specified in a given application. For example, the distance between the lower pins will be greater where a tolerance of plus or minus 1 degree is specified as opposed to a tolerance of plus or minus half a degree. Determining the relative placement of the pins is all conducted in accordance with standard trigonometric functions. While the given shape and composition of the material serving as the medium, into which the pins are transversely embedded, varies from application to application one constant is that the pins and the flat base aspect of the invention must be parallel.

The present invention possesses the advantage that all of the materials required for its manufacture are common, readily accessible and of low cost. In fact, when compared to the estimated $1500 cost to produce the prior art device, the approximate $40 production cost of the instant device seems altogether modest. Moreover, common and relatively inexpensive methods of assembly are all that is required to manufacture the device.

Another significant advantage possessed by the instant device relates to its ability to maintain calibration despite considerations of handling, transportation and the like.

Yet another, and equally important, advantage of the present device relates to the radiographic image that it produces and the relative ease with which the image can be interpreted. Specifically, the typical image created by the instant device consists of a series of three parallel lines. Because the two lower pins are placed at outer distances that define the full range of acceptable tolerance in a given application, the x-axis or transverse alignment of the head of the radiographing machine will be considered aligned where each of the three pins is separately distinguishable on the radiograph. The net effect of such alignment, as discussed above, ensures that the full depth of the weld under inspection can now be radiographed which radiograph can then be relied upon for evaluating the sufficiency of the weld seam. This ability to more easily and objectively interpret the images created by the present device has resulted in greater consistency of radiograph interpretation determinations.

The present invention is very inexpensive to manufacture, it is durable and maintains its calibration and it produces images that are easier and more objectively and consistently interpreted by technicians.

DESCRIPTION OF THE PREFERRED EMBODIMENT

Figure 1:
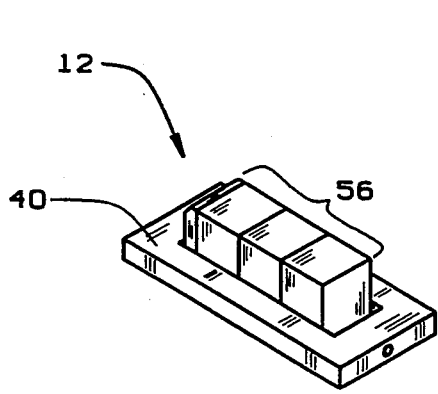
FIG. 1 is a perspective view of the prior art device.
Figure 2:
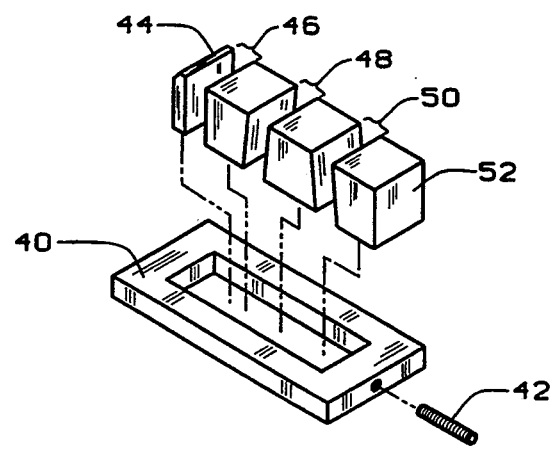
FIG. 2 is an exploded perspective view of the prior art device.
Figure 3:
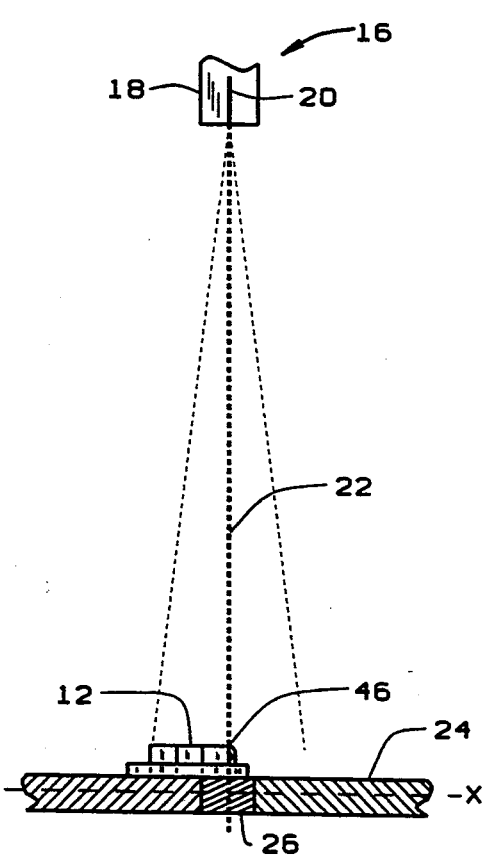
FIG. 3 is a depiction of the prior art device as it is intended to be used.
Figure 4:
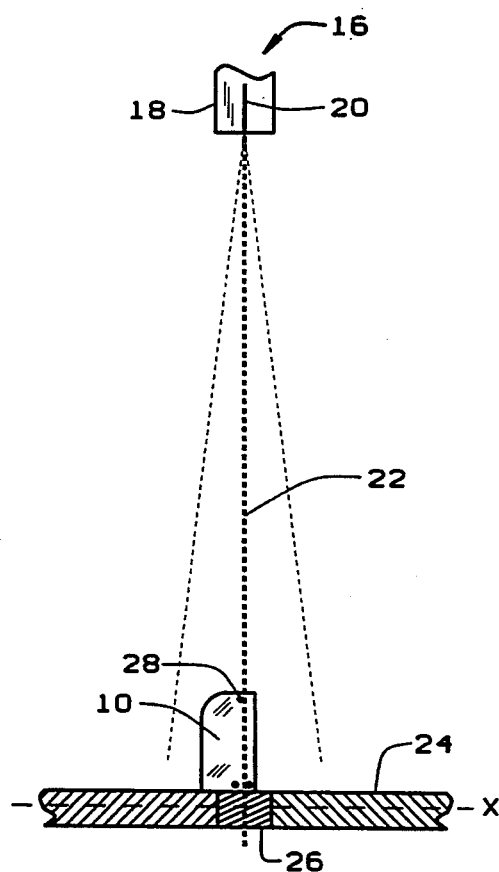
FIG. 4 depicts the preferred embodiment of the instant invention in use.

Referring now by reference numerals to the drawings and first to FIGS. 1 through 3 it will be understood that the prior art device 12 includes a series of adjacently positioned titanium blocks 56 held in position by an aluminum alloy frame 40 through one side of which set pin 42 incurs engaging the end surface of the outermost block 52 and thereby forcing the blocks 56 into close relation. The adjacent surfaces of the three blocks closest to the set pin 42 form spaces 48 and 50 which define alternating seams precision machined to within 2 degrees of taper. The fourth block 44 is characterized by a chamfered upper and outermost corner that is adjacent to the aluminum alloy frame 40 and opposite the side which surface engages the opposing side of the adjacent third block to form space 46. Space 46, while invisible to the unaided eye when device 12 is in calibration, is perpendicular to the aluminum alloy frame 40 and is intended to serve as the imaging target during alignment radiograph procedures. As shown in FIG. 3, space 46 of device 12 is positioned in the field of central ray 22 and over the median of weldment 26 included on component 24 in longitudinal relation with both the weldment and the x-ray dispersing tungsten plate 20 contained within the head 18 of the radiographing machine 16.

Figure 5:
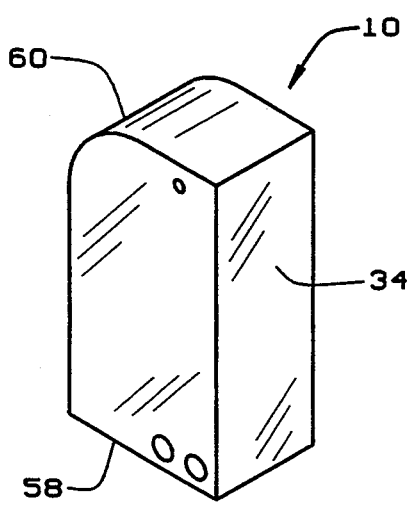
FIG. 5 is a perspective view of the preferred embodiment of the instant invention.
Figure 6:
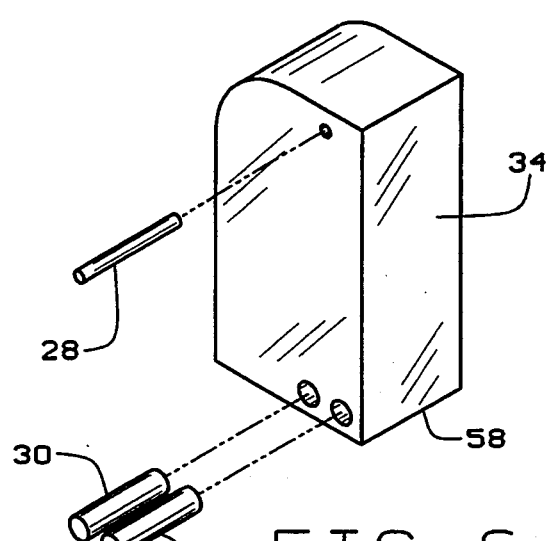
FIG. 6 is an exploded perspective view of the preferred embodiment of the instant invention.
Figure 7:
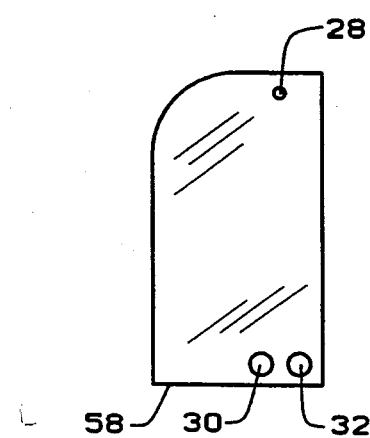
FIG. 7 is a front elevational view of the preferred embodiment of the instant invention.
Figure 8:
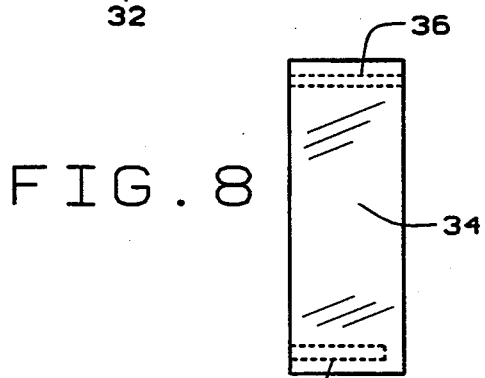
FIG. 8 is a side elevational view of the preferred embodiment of the instant invention.
Figure 9:
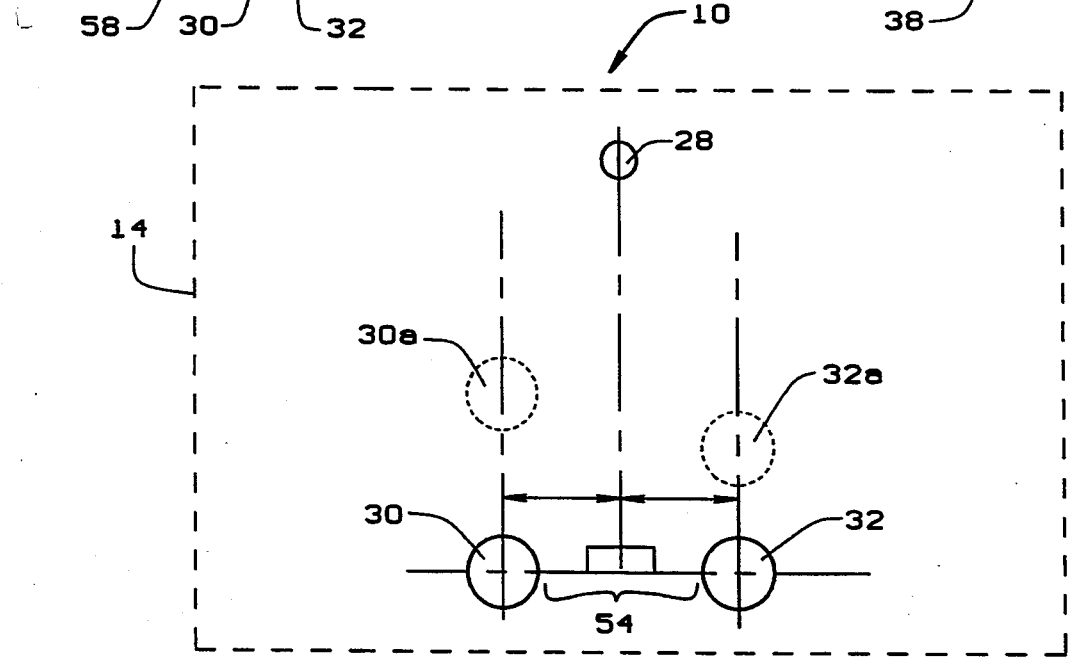
FIG. 9 is a phantom depiction illustrating both the relative arrangement of the pins employed in the instant invention and the mutable shape and composition character of the medium aspect of the invention into which the pins are transversely mounted.

Turning next to FIGS. 5 through 8 it will be understood that what is depicted is the preferred embodiment of the instant invention 10 which includes a medium 34 into which an upper pin 28 and parallel lower pins 30 and 32 are imbedded transversely and each in parallel relation to the smooth, flat base 58 of the medium 34. FIG. 5 illustrates an essentially rectangular configuration of the instant invention in which the upper outside corner 60 of the device is rounded. FIG. 6 illustrates how the pins 28, 30 and 32 are inserted into the medium 34 and also importantly shows that upper pin 28 is both longer than either of pins 30 and 32 and it is smaller in diameter. Upper pin is preferably smaller in diameter than either of the lower pins 30 and 32 so that it may readily be distinguished on radiographic film. This feature makes it easier for the technician to adjust the head of the radiographic machine when x-axis alignment falls outside prescribed tolerance. FIG. 8 reveals in phantom fashion the preferred greater length 36 of upper pin 28 as compared to the shorter lower pin length 38. The significance of this disparity in lengths resides in the technicians ability to readily discern all three pin images when superimposition of the pins occurs on the radiograph. Like the distinction in diameter, this preferred feature of the present invention makes x-axis alignment within tolerance much easier for the technician. FIG. 7 shows the midpoint placement of upper pin 28 relative to lower pins 30 and 32 and, additionally, illustrates the parallel relationship between each of the pins and the smooth, flat base 58 of the invention. Turning next to FIG. 9, it will be understood that the present invention 10 includes a medium 14 theoretically unlimited in size and shape. The figure also shows that, despite the theoretically unlimited size and shape of the medium 14, the basic configuration of the pins remains in an adjacent right triangle relationship 54. Additionally, FIG. 9 shows that, while the pins must remain in a vertically parallel relationship in order for the invention to function, a horizontal parallel relation need not be maintained provided that the adjacent right triangle relation between the three pins exists. Accordingly, phantom lower pins 30(a) and 32(a) illustrate an alternate arrangement of the lower pins 30 and 32.

As discussed supra, the specific distances between each of the pins employed in the present invention are calculated based upon specific tolerance specifications and in accordance with fundamental principles of trigonometry. In addition, in selecting suitable materials for use in the manufacture of the invention, consideration is specifically given to radiographic equivalence factors and material cost. For purposes of making the medium component of the instant invention, a durable low cost material that poorly absorbs radiation is desirable. Common suitable materials would be acrylics, polycarbonate compositions, thermoplastics and the like as well as materials like wood and even certain low grade radiation absorptive metals. The pins of the present invention should, obversely, be made of materials that are known to absorb radiation well. Materials such as steel and, in particular, stainless steel are known to readily absorb radiation and thereby create a sharp radiographic image. For this reason and because of the relative low cost, stainless steel is the preferred material in the manufacture of the pin components of this invention.

In view of the above, it will be understood that various aspects and features of the invention are achieved and other advantageous results are attained. While a preferred embodiment of the angle indicator invention has been shown and described, it will be clear to those skilled in the an that various modifications may be made without departure from the invention in its broader aspects.

I claim as my invention:

1. A device for establishing perpendicular x-axis alignment between the head of an x-ray machine and the central region of a weldment, the device comprising:
   (a) a flat base; and
   (b) a plurality of metal pins inserted transversely into said device, said pins being arranged parallel with said base and in adjacent right triangle relation with each other.

2. A device as defined in claim 1, in which there exists three pins, one upper and two lower, said upper pin being positioned central to the distance between said two lower pins.

3. A radiographic inspection aid comprising:
   a medium having a flat base; and
   a plurality of radiographically absorptive pins mounted transversely within said medium in right triangle relation to each other.

4. The inspection aid of claim 3, wherein the medium is comprised of a material having a low radiographic absorption index.

5. The inspection aid of claim 3, wherein said pins are three in number and are arranged such that a pair are disposed in parallel relation to each other adjacent said base and said third pin is disposed above and intermediate said pair of pins.

6. The inspection aid of claim 5, wherein said pair of pins are disposed parallel to said base.

7. A method for ensuring weld seam integrity comprising:
   positioning a radiographic material below said weld seam to receive an image;
   providing a support structure having a means for displaying at least a pair of visible lines on said radiographic material;
   positioning said support structure over said weld seam;
   aligning a radiation-emitting machine over said weld seam such that a central ray emitted therefrom passes through said weld seam and said support structure and is received by said radiographic material producing an image thereon;
   evaluating said image produced upon said radiographic material.

8. The method according to claim 7, wherein said support structure has a flat base and at least one upright side intersecting said base to define a corner having an outside edge.

9. The method according to claim 8, wherein said means for displaying at least a pair of visible lines comprises three pins, one upper and two lower, said upper pin being positioned intermediate said two lower pins wherein all of said pins are mounted transversely within said support structure and wherein said base is positioned over said weld seam such that said upper pin is substantially central to said weld seam.

10. The method according to claim 9, wherein said support structure is block shaped and has an arcuate corner opposite said outside edge.

11. The method according to claim 9, wherein said support structure is comprised of a material having a low radiographic absorption index.

12. The method according to claim 7, wherein said means for displaying at least a pair of visible lines comprises a plurality of pins mounted transversely within said support structure.

13. The method according to claim 12, wherein said visible lines are parallel and said pins are three in number.

14. The method according to claim 13, wherein said pins are mounted in right triangle relation to each other.

* * * * *